United States Patent
Buschbaum et al.

(10) Patent No.: US 12,220,177 B2
(45) Date of Patent: Feb. 11, 2025

(54) REFERENCE DEVICE FOR REAL-TIME TRACKING OF BONE AND/OR SURGICAL OBJECTS IN COMPUTER-ASSISTED SURGERY

(71) Applicant: AO Technology AG, Chur (CH)

(72) Inventors: Jan Buschbaum, Davos Platz (CH); Markus Windolf, Davos (CH)

(73) Assignee: AO Technology AG, Chur (CH)

( * ) Notice: Subject to any disclaimer, the term of this patent is extended or adjusted under 35 U.S.C. 154(b) by 964 days.

(21) Appl. No.: 16/967,478

(22) PCT Filed: Feb. 5, 2019

(86) PCT No.: PCT/CH2019/000001
§ 371 (c)(1),
(2) Date: Aug. 5, 2020

(87) PCT Pub. No.: WO2019/153096
PCT Pub. Date: Aug. 15, 2019

(65) Prior Publication Data
US 2021/0205022 A1    Jul. 8, 2021

(30) Foreign Application Priority Data

Feb. 7, 2018   (CH) ........................... 145/18

(51) Int. Cl.
*A61B 34/20*   (2016.01)
*A61B 34/10*   (2016.01)
(Continued)

(52) U.S. Cl.
CPC .............. *A61B 34/20* (2016.02); *A61B 34/10* (2016.02); *A61B 90/39* (2016.02); *A61B 90/57* (2016.02);
(Continued)

(58) Field of Classification Search
CPC ......... A61B 34/20; A61B 34/10; A61B 90/39; A61B 90/57
(Continued)

(56) References Cited

U.S. PATENT DOCUMENTS 5,368,030 A * 11/1994 Zinreich ................ A61B 90/39
324/309
5,904,691 A * 5/1999 Barnett .............. A61B 17/3403
606/129

(Continued)

FOREIGN PATENT DOCUMENTS

CN         205586092 U     9/2016
EP         0-832 609 A2 *  4/1998   ............. A61B 17/34
(Continued)

OTHER PUBLICATIONS

Stoll et al. (Passive Markers for Tracking Surgical Instruments in Real-Time 3-D Ultrasound Imaging, 2012, IEEE, pp. 1-44) (Year: 2012).*

(Continued)

*Primary Examiner* — Iftekhar A Khan
(74) *Attorney, Agent, or Firm* — Rankin, Hill & Clark LLP (57) ABSTRACT

Reference device (1) for real-time tracking of bone and/or surgical objects in computer-assisted surgery, the device (1) comprising: A) an upper member (2) having at least one circular cylindrical hole (3) penetrating through the upper member (2) from the upper surface (5) to the lower surface (6), wherein the hole (3) defines a circular cylindrical reference element (15) having a diameter d and a height h, the ratio between the diameter d and the height h of the reference element (15) is minimum ⅓, and B) a lower (Continued)

member (4) configured to cover the lower orifices (8) of the holes (3); and wherein C) the upper member (2) is configured as a plate shaped body.

18 Claims, 7 Drawing Sheets

(51) Int. Cl.
  *A61B 90/00* (2016.01)
  *A61B 90/57* (2016.01)
(52) U.S. Cl.
  CPC ... *A61B 2034/104* (2016.02); *A61B 2034/105* (2016.02); *A61B 2090/376* (2016.02); *A61B 2090/3966* (2016.02); *A61B 2090/3983* (2016.02)
(58) Field of Classification Search
  USPC .......................................................... 703/20
  See application file for complete search history.

(56) References Cited

U.S. PATENT DOCUMENTS

| | | | | |
|---|---|---|---|---|
| 9,987,024 | B2* | 6/2018 | Frey | A61B 17/1703 |
| 11,045,267 | B2* | 6/2021 | Hussain | A61B 34/32 |
| 11,331,150 | B2* | 5/2022 | Jascob | A61B 90/39 |
| 2002/0077543 | A1* | 6/2002 | Grzeszczuk | A61B 90/36 |
| | | | | 348/E13.008 |
| 2004/0186347 | A1* | 9/2004 | Shose | A61B 34/20 |
| | | | | 600/102 |
| 2008/0281334 | A1* | 11/2008 | Zheng | A61B 17/1703 |
| | | | | 606/97 |
| 2009/0054910 | A1* | 2/2009 | Zheng | A61B 17/1725 |
| | | | | 382/128 |
| 2009/0326579 | A1* | 12/2009 | Anderhub | A61B 17/0401 |
| | | | | 606/232 |
| 2011/0028831 | A1* | 2/2011 | Kent | A61B 90/39 |
| | | | | 600/426 |
| 2011/0213379 | A1* | 9/2011 | Blau | A61B 17/1717 |
| | | | | 703/11 |
| 2013/0072784 | A1* | 3/2013 | Velusamy | A61B 18/02 |
| | | | | 600/424 |
| 2014/0343572 | A1* | 11/2014 | Windolf | A61B 34/20 |
| | | | | 606/130 |
| 2016/0267659 | A1* | 9/2016 | Vasey | A61B 90/39 |
| 2017/0105802 | A1* | 4/2017 | Taraschi | A61B 34/20 |
| 2017/0258526 | A1* | 9/2017 | Lang | A61B 17/157 |

FOREIGN PATENT DOCUMENTS

| | | | | |
|---|---|---|---|---|
| WO | WO-2007051304 A1 * | 5/2007 | | A61B 19/00 |
| WO | 2013086642 A1 | 6/2013 | | |
| WO | 2016139557 A1 | 9/2016 | | |
| WO | WO-2019153096 A1 * | 8/2019 | | A61B 34/10 |

OTHER PUBLICATIONS

International Search Report dated Apr. 17, 2019 filed in PCT/CH2019/000001.

* cited by examiner

REFERENCE DEVICE FOR REAL-TIME TRACKING OF BONE AND/OR SURGICAL OBJECTS IN COMPUTER-ASSISTED SURGERY

BACKGROUND OF THE INVENTION

1. Field of the Invention

The invention relates to a reference device for real-time tracking of bone and/or surgical objects in computer-assisted surgery, to a tracking system for real-time tracking of bone and/or surgical objects in computer-assisted surgery and to a method for real-time tracking of bone and/or surgical objects in computer-assisted surgery.

In computer-assisted surgery, particularly in the field of orthopedics systems for tracking, navigation and manipulation applications of e.g. bone fragments, surgical instruments, tools and/or implants are commonly used. Many of these devices are based on the use of radiographic devices. Shortcomings of these systems are the considerable radiation doses to which the patient and the operation staff are subjected to and that these systems allow only static position tracking without real-time feedback.

2. Description of the Related Art

A reference device to be used with an optical sensor apparatus associated with a CAS system is known from WO 2007/051304 JUTRAS ET AL. This known tracker device comprises a support having a plurality of circular openings, wherein retro-reflective surfaces are positioned in the openings so as to form circular optical elements. The support can be cast in metal or molded in plastic while the retro-reflective surfaces comprise a retro-reflective material so as to be detectable by an optical sensor apparatus associated to a CAS system. A drawback of this known reference device is the complex structure of the support of the reference device, particularly the configuration and arrangement of the connectors by means of which the support is securable to a surgical instrument so that corresponding connecting means arranged at the surgical instrument are required. Due to its complex structure the reference device cannot be easily integrated in medical implants, surgical instruments and/or surgical tools. Furthermore, this known reference device is not designed for using intraoperative C-arm images.

BRIEF SUMMARY OF THE INVENTION

It is an object of the invention to provide a reference device which has a simple structure and which can be attached to a medical implant, surgical instrument and/or surgical tool without requiring connectors having a specific geometry.

The invention solves the posed problem with a reference device for real-time tracking of bone and/or surgical objects as disclosed herein, with a tracking system for real-time tracking of bone and/or surgical objects as disclosed herein and with a method for real-time tracking of bone and/or surgical objects in computer-assisted surgery as disclosed herein.

The advantages of the reference device according to the invention are essentially that:

the reference device can be attached to a medical implant, surgical instrument and/or surgical tool (e.g. a guide wire, drill-sleeve, Schanz-pin etc.) by using a simple clamp, or can be clipped on a surgical instrument or tool. By this means the reference device may be attached to a bone via the guide wire so as to permit to reference the relative position between the attached reference device and anatomical structures (e.g. a bone, bone fragments, joints) and/or the relative position between several reference devices using a radiographic image and thus to enable a subsequent tracking by means of photographs or video recording. Alternatively, the reference device can be integrated in implants, surgical instruments and/or tools; and the configuration of the reference elements permits to determine the spatial position of the reference device in situ on the basis of 2-dimensional (2D) images, including photographs, video records or (medical) 2D X-ray images; this means particularly that a single 20 image is sufficient to determine the 3-dimensional spatial position and orientation of the reference device in accordance with the present invention. More specifically, compared to methods and devices known in the state of the art, a stereo-optical image acquisition (i.e. using at least two differently positioned image acquisition devices like cameras) is not required for determining the 3-dimensional positioning. In another embodiment of the invention, one and the same reference device allows the determination of the spatial position on the basis of photographic as well as x-ray images.

Further advantageous embodiments of the invention can be commented as follows:

In a special embodiment the upper member comprises a radiopaque material at least at the periphery of each hole.

In a further embodiment the reference device comprises attachment means to loosenably secure the reference device to a medical implant, surgical instrument and/or surgical tool or to an operation table. The advantages of this configuration are essentially that the reference device can be attached to existing/ordinary surgical objects, instruments etc. The tracking of these objects is therefore possible. Standard instruments can be used. The reference device is attachable to different objects, instruments and can therefore be used for a plurality of different applications.

In again another embodiment the reference device is integrated in a medical implant, a surgical instrument and/or surgical tool. This configuration permits the advantages of a reference device with a smaller size which does not interfere with the surgical procedure and which is secure against loosening. Furthermore, no additional reference device is needed.

In a further embodiment the attachment means are configured as a clamp or clip or a threaded connection. By this means the advantages can be achieved that the reference device can be easily attached and detached and can be used for a plurality of different objects.

In a further embodiment the reference device comprises a locking mechanism to position and secure the reference device in a defined position relative to a medical implant, a surgical instrument and/or surgical tool. Due to the locking mechanism the reference device is easy to position in a defined location and is secured against displacement and rotation.

In a further embodiment the lower member has an upper surface which has different a color and/or reflectance than the upper member. This configuration permits the advantage that for color based detection of the visible surface boundaries of the lower member in video or image data using standard image processing methods the lower member is visually distinctive from the upper member so as to distinguish the bottom of the holes from the upper member.

In again a further embodiment the lower member is reflective or luminescent, preferably fluorescent or phosphorescent. By this means the visibility of the lower member in video or image data is enhanced so as to ease hole detection and image processing.

In another embodiment the lower member is attached to the lower surface of the upper member. Due to the lack of space between the upper and lower member the reference device is easier to manufacture and easier to clean.

In yet another embodiment the lower member is offset to the lower surface of the upper member. The space between the lower surface of the upper member and the lower member allows light to penetrate and to illuminate the lower member.

In a further embodiment the lower member has a recess each in the range of the lower orifice at the lower surface of the upper member, wherein the recess has a concave shape, preferably a parabolic shape. Due to the curved (e.g. parabolic) surface of the recess the advantage of a better representation of the contour of the lower orifice can be achieved.

In a further embodiment the upper member comprises an intermediate member which is arranged between a lower surface of the upper member and the lower member, wherein the intermediate member is made from a transparent material. This configuration permits the advantage that the transparent material between the upper and lower member allows light to penetrate and to illuminate the lower member.

In a further embodiment the lower member is circular cylindrical and is attached to the inner wall of the hole at the proximity of the lower orifice of the hole. This configuration permits the advantages of a smaller size of the reference device as well as a configuration which is easier to manufacture and to clean.

In a further embodiment the diameter d of the reference elements and the diameter of the holes is minimum 3 mm. Holes with smaller diameters cannot be detected robustly. This is a function of image resolution of video, photo and X-ray devices.

In a further embodiment the reference device comprises a plurality of holes, wherein each hole defines a circular cylindrical reference element having a diameter d and a height h. This configuration permits the advantage that the robustness of the calculation of the spatial position in 6 degrees-of-freedom increases with the number of holes. Furthermore, circular cylindrical holes are easy to manufacture.

In another embodiment one or more holes have a run-out section at the upper and/or lower orifice of the hole, which is preferably configured as a chamfer or a fillet. At larger tilting angles of the hole axes with respect to the X-ray beam the use of x-ray blurs out the hole contours leading to underestimation of the calculated angles. Due to the chamfer or fillet the advantage can be achieved that material is added on the path of the rays so as to reduce the blurring effect leading to a more accurate estimation in the case of larger tilting angles.

In another embodiment the lower member is made of a translucent material. Due to this configuration light can penetrate for enhancement of the representation of the contour of the lower orifice of the holes.

In another embodiment the central axis of at least one hole is skew to the central axes of the other holes. By this means the robustness of the calculated orientation of the reference device can be increased due to avoiding false local minima in the solution space.

In again another embodiment the upper member is made of medical grade material, preferably stainless steel, titanium or plastic. Therewith the use with X-ray imaging is permitted.

In another embodiment the upper member and the lower member are formed out of one piece, with the proviso that the at least one circular cylindrical hole is a blind hole. The bottom of the blind hole can have a concave shape, preferably a parabolic or conical shape. The bottom of said blind hole forms a surface corresponding to the lower surface.

In a special embodiment of the tracking system the surgical object is a medical implant, surgical instrument or surgical tool, preferably one of a guide wire, a Schanz-pin, a drill sleeve, a Kirschner-wire, a surgical power drill, a bone screw or a guide-block or an insertion handle.

In a further embodiment of the tracking system the camera device is one of a photo camera, a video camera and an infra-red camera.

According to a further aspect of the invention a method for real-time tracking of bone and/or surgical objects in computer-assisted surgery is provided, wherein the method comprises the steps: (I) temporarily positioning at least one medical implant, surgical instrument and/or surgical tool equipped with a reference device according to the invention with respect to an anatomical structure; (II) capturing the at least one reference device by means of a photo/video camera device in at least one medical image; (III) calculating the spatial orientation and position of the at least one reference device with respect to a camera based system of coordinates using data from the medical image; (IV) transforming the derived orientation and position into a local system of coordinates; and (V) transmitting the derived orientation and position information to a display means, wherein step (III) comprises the sub-steps of:
  (i) automatically detecting a lens-shaped projection of a cylindrical reference element arranged in the at least one reference device and determining of significant landmarks by use of image processing algorithms;
  (ii) simulating a virtual geometric representation of the cylindrical reference element and of virtual projection points corresponding to the landmarks;
  (iii) iteratively optimizing the angular orientation and position of the virtual geometric representation by means of a numerical optimization routine to determine the actual spatial position and orientation of the cylindrical reference element;
  (iv) calculating the spatial orientation and position of the at least one reference device by finding a unique solution for a system of cylindrical reference means.

In a special embodiment of the method step II) additionally involves taking at least one X-ray image of the at least one reference device and the anatomical structure.

In another embodiment of the method step II) involves obtaining the medical image by capturing the screen of a medical radiographic device by using a photo/video camera.

In another embodiment of the method step IV) additionally involves establishing an anatomy based system of coordinates based on the at least one X-ray image.

In again another embodiment of the method step IV) involves transforming the orientation and position of a reference device into a system of coordinates defined by the orientation and position of a second reference device.

In a further embodiment of the method step IV) involves transforming the orientation and position values of the at least one reference device into an anatomy based system of coordinates.

In a further embodiment of the method step IV) involves transforming the orientation and position values of the at least one reference device into a system of coordinates derived from an earlier iteration step of the method according to invention.

In yet a further embodiment of the method steps II)-IV) are iteratively repeated to create redundant information.

In another embodiment of the method the display means in step V) is a screen which is integrated in one of a smartphone, a tablet computer, a smart glass, a personal computer and a head mounted display.

In another embodiment of the method the implant position is visualized by augmenting the X-ray image with a geometric representation of an implant in its current position.

In another embodiment of the method step III) is repeated after changing the view angle of the medical image.

In a further embodiment of the method the local system of coordinates of the anatomical structure is established by manually selecting anatomical landmarks.

In a further embodiment the method includes the additional step of measuring angles between bone fragments during a surgical fracture reduction or during corrective osteotomies.

In again a further embodiment of the method the camera device is attached to or integrated in one of a surgical instrument, a surgical power drill, an X-ray device, an OR-light, a smartphone, a tablet computer, a smart glass and a head mounted display.

A BRIEF DESCRIPTION OF THE DRAWINGS

Several embodiments of the invention will be described in the following by way of example and with reference to the accompanying drawings in which.

DETAILED DESCRIPTION OF THE INVENTION

As used in this application the term "landmark" has the meaning of a distinctive feature marking a particular location of an object, e.g. detectable anatomical landmarks like a hole, a vertex, an edge or spherical aspects, for instance a femoral head.

Furthermore, as used herein, the singular form "a", "an" and "the" does not exclude plural references unless the context clearly dictates otherwise. For example, the term "a cylindrical reference element" or "at least one cylindrical reference element" or "a medical image" does not exclude a plurality of cylindrical reference elements or a plurality of medical images.

Figure 1:
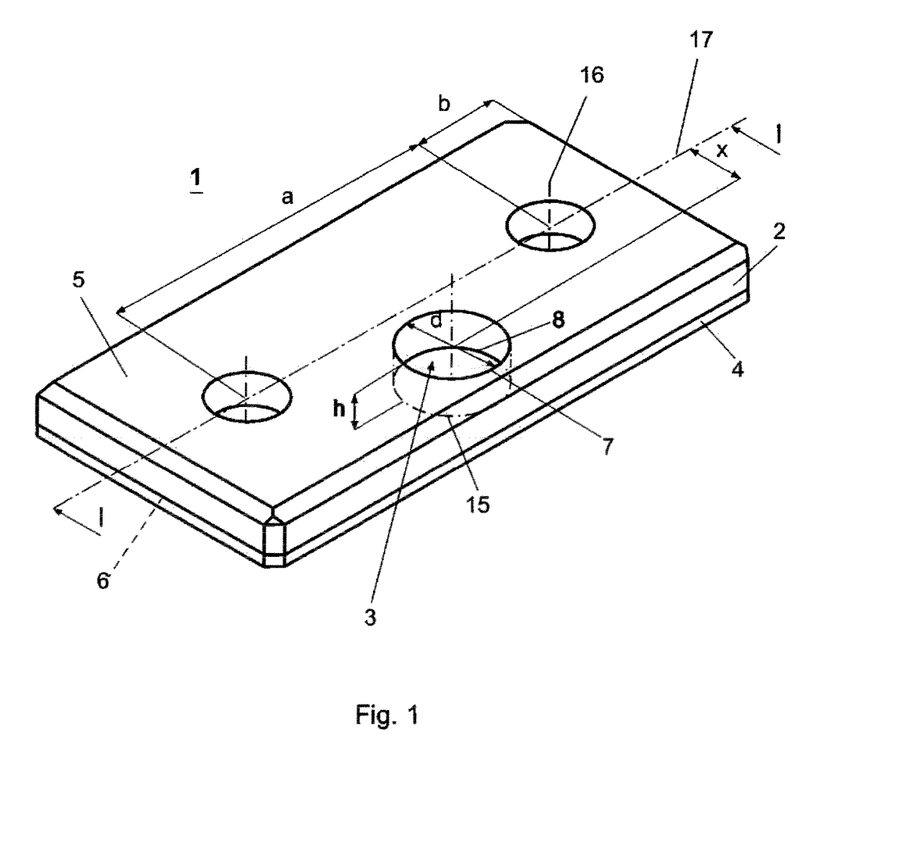
FIG. 1 illustrates a perspective view of an embodiment of the reference device according to the invention.
Figure 2:
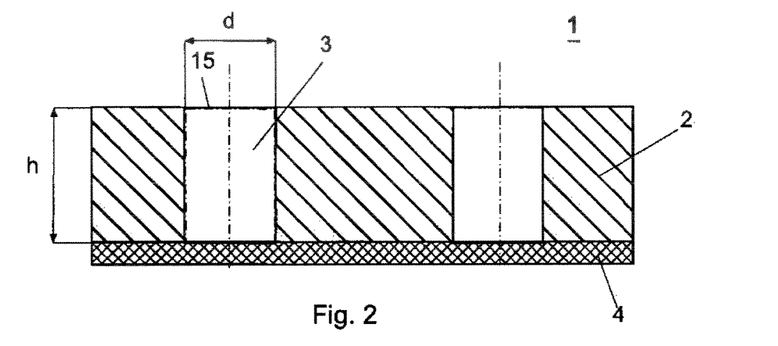
FIG. 2 illustrates a sectional view of the embodiment of FIG. 1 along line I-I in FIG. 1.
Figure 3:
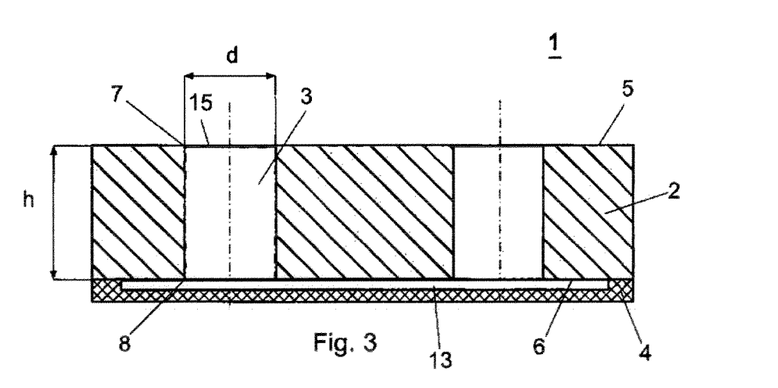
FIG. 3 illustrates a longitudinal section of another embodiment of the reference device according to the invention.

FIGS. 1 and 2 illustrate, exemplarily but not limiting, an embodiment of the reference device 1 according to the invention including a planar plate shaped upper member 2 having an upper surface 5, a lower surface 6 and three holes 3 penetrating through the upper member 2 from the upper surface 5 to the lower surface 6 so that each hole 3 has an upper orifice 7 at the upper surface 5 and a lower orifice 8 at the lower surface 6 and a lower member 4 attached to the lower surface 6 of the upper member 2. The lower member 4 is made of a radiolucent material and configured to cover the lower orifices 8 of the holes 3. The upper member 2 can have the shape of a rectangular parallelepiped, or a prismatical or cylindrical form. Alternatively, the lower member 4 can be separated from the lower surface 6 of the upper member 2 by a gap 13 as illustrated in FIG. 3. The upper member 2 is made of a radiopaque material, e.g. medical grade stainless steel. The surface of the upper member 2 can have any color and can be matt or transparent.

Figure 9:
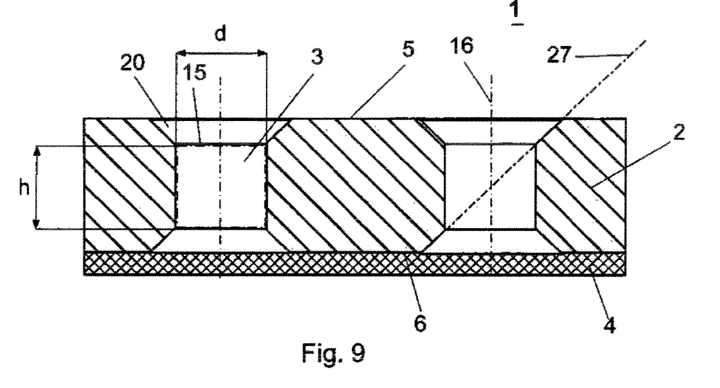
FIG. 9 illustrates a longitudinal section of yet a further embodiment of the reference device according to the invention.

The holes 3 are cylindrical with known diameter, depth and arrangement. Each of the holes 3 has a central axis 16 extending perpendicularly to the upper surface 5 of the upper member 2. In alternative embodiments, the central axis 16 of at least one hole 3 can be skew, e.g. 5° with respect to the central axes 16 of the other holes 3. The internal surfaces of the holes 3 can be matt varnished in order to avoid light reflections and/or can be of different color than the outer surface of the upper member 2. The holes 3 have a diameter of minimum 3 mm. Each hole 3 defines a circular cylindrical reference element 15 having a diameter d coinciding with the diameter of the hole 3 and a height h measured between the upper orifice 7 and the lower orifice 8, wherein the ratio between the diameter d and the height h of the reference element 15 is minimum ⅓. Exemplarily, but not limiting, the reference device 1 can comprise a plurality of holes 3, wherein each hole 3 has a different diameter d as illustrated in FIG. 9. Alternatively, the diameter d of the holes 3 can be equal.

The plate shaped upper member 2 has a longitudinal axis 17 and—when viewed with respect to the longitudinal axis 17—the outer two of the three holes 3 are arranged in such a way that their central axes 16 cut the longitudinal axis 17 of the upper member 2 with a minimum distance of 10 mm while the third hole 3 is arranged between the outer two holes 3 and with an offset x to the longitudinal axis 17 of the upper member 2. The two outer holes 3 are arranged in such a way that between the periphery of each hole 3 and the periphery of the upper member 2 a wall thickness b of minimum 1.5 mm remains.

The lower member 4 is made of any radiation permeable material (e.g. plastic) and can have any color, can be matt, reflective and/or partially transparent so as to be visually distinguishable from the upper member 2. In further embodiments the lower member 4 can be luminescent (fluorescent, phosphorescent) or can be illuminated by a mirror, light reflecting material or by artificial light (e.g. by using LEDs). The shape of the lower member 4 is flat, but can alternatively be curved or both. In an alternative embodiment, the reference device 1 comprises a lower member 4 for each hole 3, wherein each lower member 4 is configured as a circular cylindrical plug attached to the cylindrical inner wall of the hole 3 at the proximity of the lower orifice 8 of the hole 3. In this case the height h of the reference element 15 is limited by the upper orifice 7 of the hole 3 and an upper surface of the plug shaped lower member 4.

FIG. 3 illustrates an alternative embodiment or the reference device 1 according to the invention which differs from the embodiment of FIGS. 1 and 2 only therein that the lower member 4 is separated from the lower surface 6 of the upper member 2 by a gap 13 in the range of the holes 3. The reference elements 15 each have a diameter d coinciding with the diameter of the respective hole 3 and the height of each reference element 15 is limited by the respective upper and lower orifices 7, 8 of the holes 3.

Figure 4:
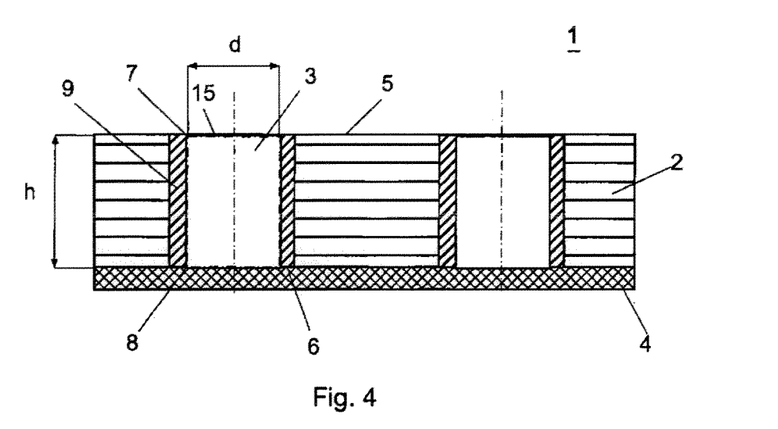
FIG. 4 illustrates a longitudinal section of a further embodiment of e reference device according to the invention.

A further embodiment of the reference device 1 according to the invention is illustrated in FIG. 4 which differs from the embodiment of FIGS. 1 and 2 only therein that the upper member 2 comprises radiopaque sleeves 9 surrounding the holes 3 and extending from the upper surface 5 to the lower surface 6 of the upper member 2. The remaining part of the upper member 2 is made of a radiolucent material. The lower member 4 can be attached to the lower surface 6 of the upper member 2 as illustrated in FIGS. 1 and 2 or can alternatively be separated from the lower surface 6 of the upper member 2 by a gap 13 as illustrated in FIG. 3.

Figure 5:
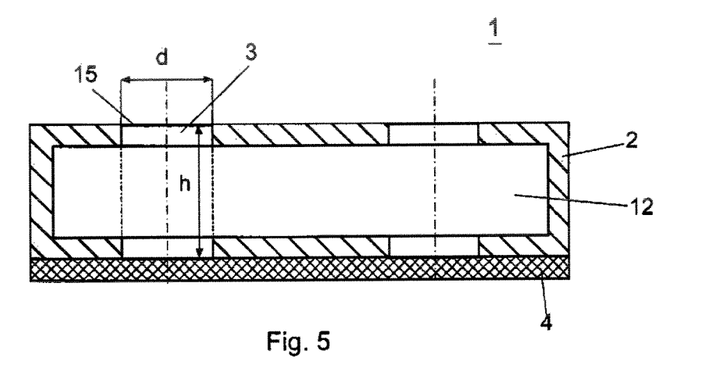
FIG. 5 illustrates a longitudinal section of another embodiment of the reference device according to the invention.
Figure 6:
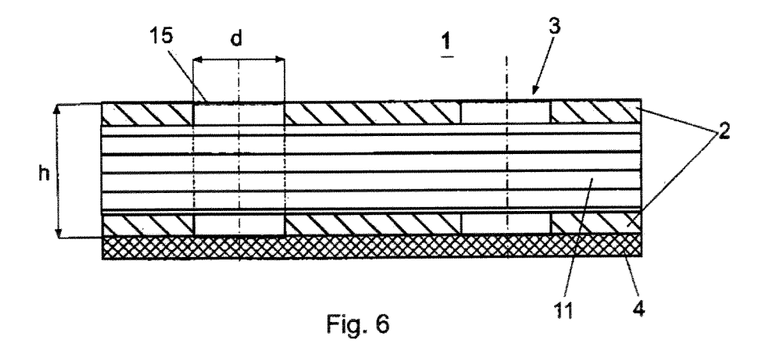
FIG. 6 illustrates a longitudinal section of a further embodiment of the reference device according to the invention.

FIG. 5 illustrates an embodiment of the reference device 1 according to the invention which differs from the embodiment of FIGS. 1 and 2 only therein that the upper member 2 comprises a hollow space 12 covered by an upper and a lower material portion. The holes 3 penetrate through the upper and lower material portions and define reference elements 15 which have a diameter d coinciding with the diameter of the respective hole 3 and which have a height h that is limited by the upper orifice 7 of the respective hole 3 at the upper surface 5 of the upper member 2 and by the lower orifice 8 of the respective hole 3 at the lower surface 6 of the upper member 2. Alternatively, as illustrated in FIG. 6 an intermediate layer 11 can be positioned between the upper and lower material portion of the upper member 2 or alternatively between the lower surface 6 of the upper member 2 and the lower member 4. The intermediate layer 11 is made of a radiolucent and transparent material.

Figure 7:
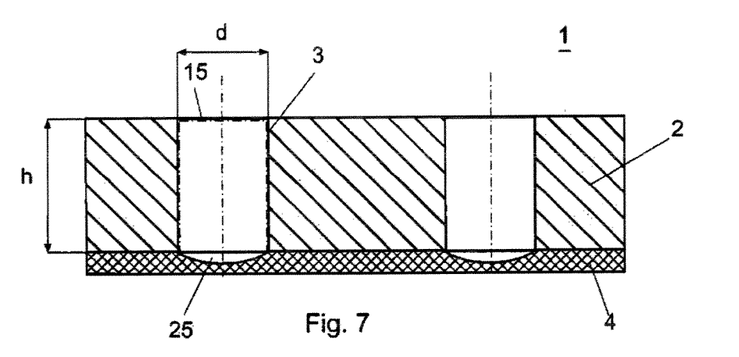
FIG. 7 illustrates a longitudinal section of a further embodiment of the reference device according to the invention.

FIG. 7 illustrates a further embodiment of the reference device 1 according to the invention which differs from the embodiment of FIGS. 1 and 2 only therein that the lower member 4 has a recess 25 each in the range of the lower orifice 8 at the lower surface 6 of the upper member 2, wherein the recess 25 has a concave shape, preferably a parabolic shape so as to permit a better representation of the contour of the lower orifice.

Figure 8:
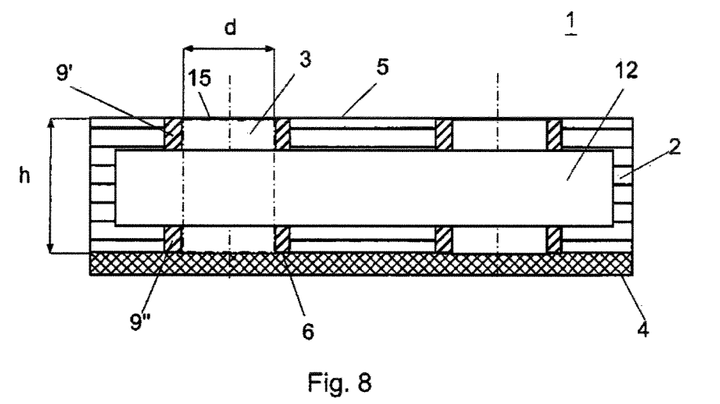
FIG. 8 illustrates a longitudinal section of again a further embodiment of the reference device according to the invention.

A further exemplary embodiment of the reference device 1 according to the invention is illustrated in FIG. 8. The embodiment of FIG. 8 is a combination of the embodiments of FIGS. 4 and 5 and differs from FIG. 4 only therein that each of the radiopaque sleeves 9 according to FIG. 4 is divided into two separate radiopaque sleeve sections 9', 9''', wherein the first sleeve section 9' extends from the upper surface 5 to the hollow space 12 and the second sleeve section 9''' extends from the lower surface 6 to the hollow space 12. By means of the first and second sleeve sections 9', 9''' surrounding one hole 3 outside the hollow space 12 a reference element 15 is defined which has a diameter d coinciding with the inner diameter of the first and second sleeve sections 9', 9''' and a height h coinciding with the height of the upper member 2.

FIG. 9 illustrates another embodiment of the reference device 1 according to the invention which differs from the embodiment of FIGS. 1 and 2 only therein that the holes 3 comprise a run-out section at both orifices 7, 8 wherein the run-out section can be configured as a chamfer 20 or fillet each in the range of the upper surface 5 and in the range of the lower surface 6. Due to the chamfers 20 each hole 3 defines a cylindrical reference element 15 having a diameter d coinciding with the hole diameter and a height h limited by the upper and lower transitions from the respective chamfer 20 to the hole 3. The holes 3 including chamfers 20 as illustrated in FIG. 9 are exemplarily, but not limiting, added to the embodiment of FIGS. 1 and 2 but can be used in any of the embodiments illustrated in FIGS. 1-8. At larger tilting angles of the central axes 16 of the holes 3 with respect to the X-ray beam 27 the use of x-ray blurs out the hole contours leading to underestimation of the calculated angles. The chamfer 20 or fillet provides material along the path of the X-ray beam 27 so as to reduce the blurring effect leading to a more accurate estimation in the case of larger tilting angles.

Figure 10:
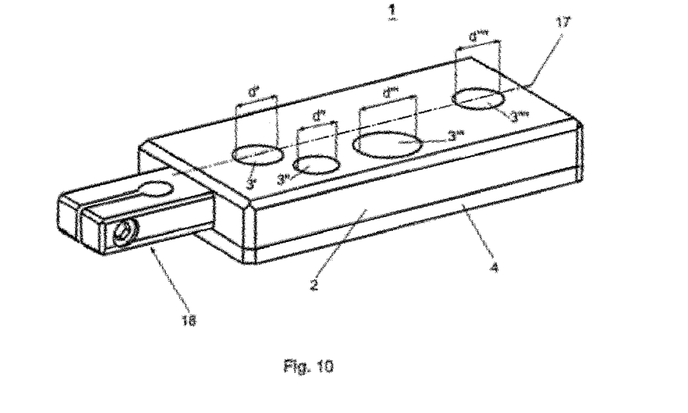
FIG. 10 illustrates a perspective view of another embodiment of the reference device according to the invention.

A further embodiment of the reference device 1 according to the invention is illustrated in FIG. 10 which differs from the embodiment of FIGS. 1 and 2 only therein that it comprises attachment means 18 to temporarily fix the reference device 1 to a cylindrical object (e.g. a guide wire) secured to a bone, a medical implant, surgical instrument and/or surgical tool or even to an operation table. The attachment means 18 are exemplarily, but not limiting, configured as a clamp projecting along the longitudinal axis 18 of the upper member 2 from one end of the upper member 2. Alternatively, the reference device 1 can be directly integrated in a surgical instrument, tool and/or implant. The medical implant, surgical instrument and/or surgical tool can exemplarily be one of a guide wire, a Schanz-pin, a drill-sleeve, a Kirschner-wire, a surgical power drill, a bone screw or a guide block. Furthermore, the embodiment of FIG. 10 exemplarily comprises a number of four holes 3', 3'', 3''', 3'''' with different diameters d', d'', d''', d''''. Each hole 3', 3'', 3''', 3'''' defines a circular cylindrical reference element 15 having a diameter d coinciding with the diameter of the respective hole 3', 3'', 3''', 3'''' and a height h measured between the upper orifice 7 and the lower orifice 8 (FIG. 1).

Figure 11:
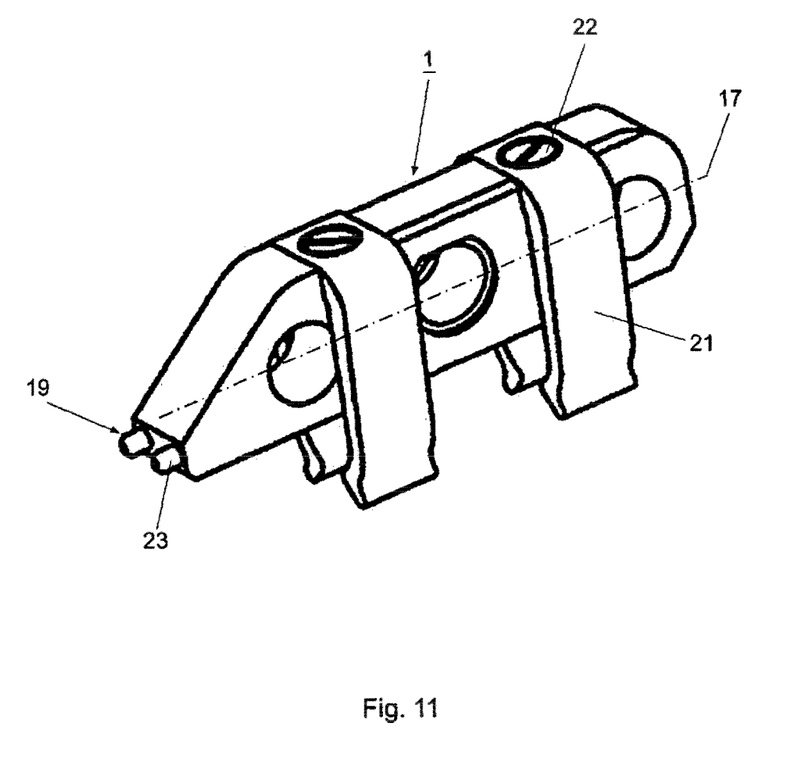
FIG. 11 illustrates a perspective view of again another embodiment of the reference device according to the invention.

An alternative configuration of the attachment means 18 which are affixed to the reference device 1 according to the invention is illustrated in FIG. 11. The attachment means 18 of FIG. 11 comprise two clips 21 attached to the reference device 1 by means of screws 22 which are screwed into screw holes (not shown) arranged on one of the sides running in the direction of the longitudinal axis 17 of the upper member 2 of the reference device 1 so that the clips 21 permit to secure the reference device 1, e.g. to a cylindrical object (e.g. a guide wire) with the longitudinal axis 17 of the upper member 2 of the reference device 1 extending essentially parallel to a longitudinal axis of the cylindrical object. Furthermore, the reference device 1 of FIG. 11 comprises a locking mechanism 19 arranged at one end of the reference device 1. The locking mechanism 19 comprises two pins 23 extending essentially parallel to the longitudinal axis 17 of the upper member 2 so that the locking mechanism 19 permits to position and secure the reference device 1 in a defined position relative to a medical implant, a surgical instrument and/or surgical tool.

An embodiment of a tracking system according to the invention comprises one or more reference devices 1 as specified above, a conventional photo/video camera, a processing unit, e.g. the central processing unit (CPU) of a computer or the processor a tablet or other digital data processing device and a display, wherein the processing unit is provided with an image processing algorithm including, exemplarily but not limiting, the numerical procedure specified below. The reference device 1 according to the invention can be attached to bone, bone fragments, surgical instruments and tools and serves as a marker for computation of the spatial position and orientation of the same in all six degrees of freedom. Due to the specified geometry and dimension of the reference element 15 (size of the hole 3) and/or the particular arrangement of the holes 3 (distance, offset) the spatial location of the reference device 1 can be determined by detecting lens-shaped projections of the holes 3 in a 2D image. The reference device 1 is designed in such a way that these projections are detectable in radiographs and in images which are captured by an ordinary optical camera device (e.g. video camera, smartphone, smart glasses etc.). This offers the opportunity of continuous real-time motion tracking without radiation via a standard video/photo camera or infra-red camera. Further, anatomical structure/ landmarks can be selected in radiographic images and registered in relation to the reference device 1. Manipulation and movements of any objects attached to a reference device 1 can then be tracked by detecting the reference device 1 in a video stream.

Figure 12:
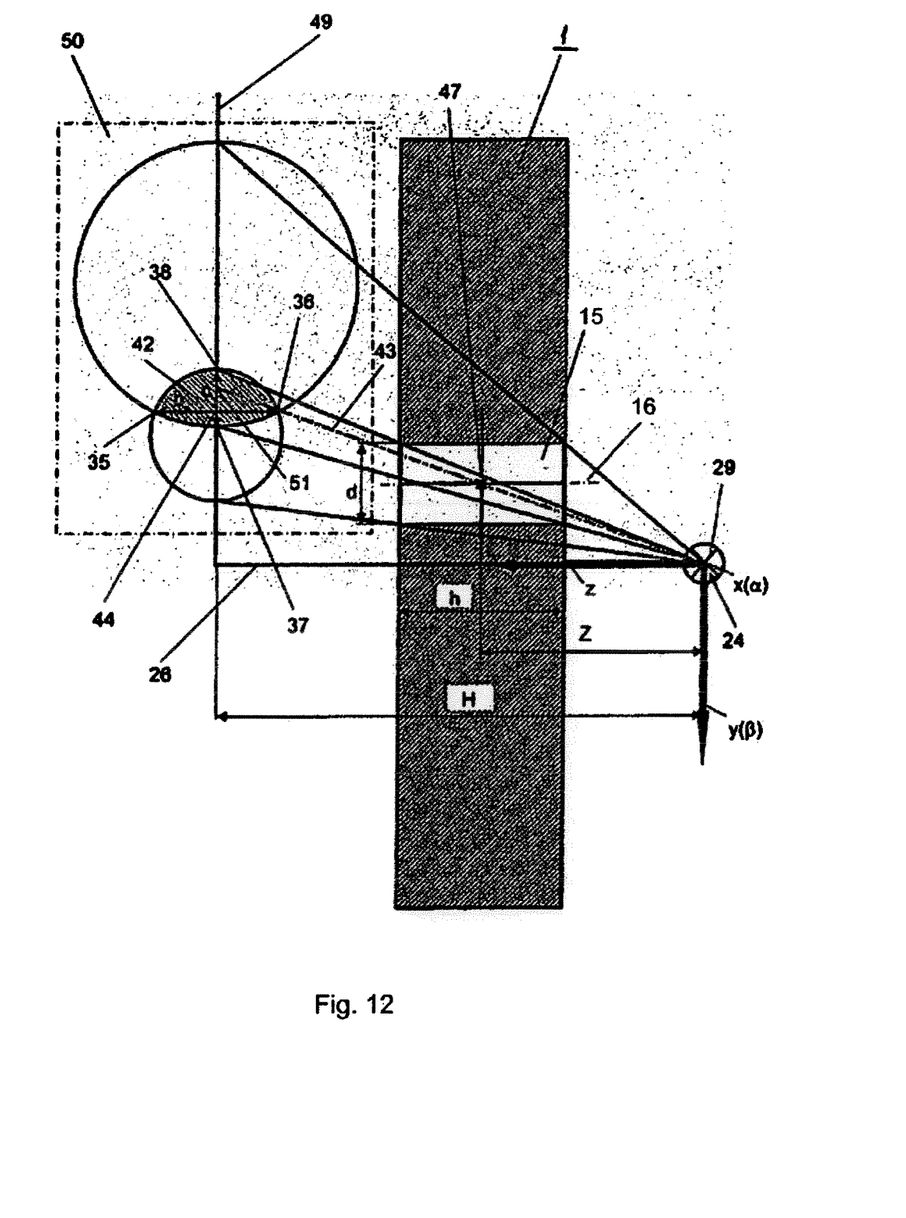
FIG. 12 illustrates a schematic representation of a central perspective of a reference element used in each embodiment of the reference device according to the invention as disclosed in WO 2013/086642 A1.

A particular method and numerical procedure for determining the spatial location of the reference device 1 by detecting lens-shaped projections of the holes 3 in a 2D image is disclosed in WO 2013/086642 AO TECHNOLOGY AG. The following part of the disclosure of WO 2013/086642 is therefore incorporated herein (the terms "reference means 16" and "medical device 1" have been changed to "reference element 15" and "reference device 1"):

FIG. 12 illustrates the steps performed for determining the position of a circular cylindrical reference element 15 in a reference device 1 according to FIGS. 1-11. Said circular cylindrical reference element 15 can be configured as a bore hole so that the cylindrical reference element 15 has a lower density than the surrounding material of the reference device 1. The cylindrical reference element 15 has a longitudinal axis coinciding with the central axis 16 of the hole, a diameter d, a height h and a centre 47. In particular said steps comprise:

A) acquiring one single medical image 50 (schematically illustrated in the drawing plane of FIG. 11) with a lens-shaped projection 42 of the cylindrical reference element 15 by means of a radiographic device including an ideally punctual energy emitting source 29 with a central ray 26 and a receiving device with an image sensor. The angulation range between the central ray 26 and the longitudinal axis of the cylindrical reference element 15 is restricted in a way that a projection 42 of the cylindrical reference element 15 must be visible on the medical image 50;

B) determining the position and orientation of the cylindrical reference element 15 from said single medical image 50 using a numerical procedure executed with said computer (or other processing unit), wherein said numerical procedure essentially comprises the steps of:

a) automatic detection of said lens-shaped projection 42 of said cylindrical reference element 15 in said medical image 50 and determination of the projection points of the two points of intersection 35, 36 and the first and second apex 37, 38 of said lens-shaped projection 42 of said cylindrical reference element 15;

b) generating a virtual geometric representation of said cylindrical reference element 15, with said diameter d, said longitudinal axis, said center 47 and said height h;

c) determining virtual projection points representing said two points of intersection 35, 36 and said first and second apex 37, 38 using said virtual geometric representation of said cylindrical reference element 15 depending on the orientation and position of the virtual geometric representation of the cylindrical reference element 15;

d) iterative determination of the position and angular orientation of said cylindrical reference element 15 by matching said virtual projection points of said virtual geometric representation of said cylindrical reference element 15 with said two points of intersection 35, 36 and said first and second apex 37, 38, wherein said cylindrical reference element 15 has three degrees of freedom:

a position Z on the z-axis of a local system of coordinates 24 measured between the center of said energy emitting source 29 and said center 47 of the cylindrical reference element 15. Said virtual geometric representation of said cylindrical reference element 15 can slide along the center line 43 determined by the center of projection 44 and the center of said energy emitting source 29. Said center of projection 44 is an approximation of the center-line projection 51 for h/H→0. The coordinates x and y of the cylindrical reference element 15 can be uniquely derived for each Z position. Therefore, one cylindrical reference element 15 determines five degrees of freedom but the algorithm needs only three degrees of freedom;

an angle α between said longitudinal axis and said center line 43 measured in the y-z plane of said local system of coordinates 24 which is fix with respect to the radiographic device; and an angle β between said longitudinal axis and said center line 43 measured in the x-z plane of said local system of coordinates 24.

The above mentioned numerical procedure includes a numerical approach for calculating the position of the cylindrical reference element 15 and is based on the following mathematical relationships:

Numerical Approach to Determine the Spatial Position and Orientation of Circular Cylindrical Reference Means The procedure relates to the mathematical condition that the projection of the radiographic device is based on an idealized central perspective. A punctiform X-ray source used as energy emitting source 29 sends rays from an origin of known distance H to the projection plane 49.

The procedure incorporates the following fundamental steps:

1. Automatic detection of the lens-shaped projection 42 of said cylindrical reference element 15 in said medical image 50 and determination of significant landmarks, i.e. two points of intersection 35, 36 and the first and second apex 37, 38 of the lens-shaped projection 42 of said cylindrical reference element 15 by use of image processing algorithms. Assumption: With h/H→0 the center-line projection 51 approximates to the center of projection 44.

2. Simulation of a virtual geometric representation of said cylindrical reference element 15 and of virtual projection points corresponding to the above mentioned landmarks.

3. Iterative optimization of the angular orientation and position of said virtual geometric representation by means of a numerical optimization routine to determine the actual spatial position and orientation of the cylindrical reference element 15.

It should be understood that if the described procedure is performed on a single circular cylindrical reference element 15, five degrees of freedom can be obtained, since the cylindrical reference element 15 is rotation symmetric. Using two or more cylindrical reference elements 15 allows constraining an object in 6 degrees of freedom.

Iterative Determination of the Orientation of the Cylindrical Reference Means or of a Set of Cylindrical Reference Means A virtual geometric representation of said cylindrical reference element 15 is generated with the known attributes d (diameter) and h (height). The virtual geometric representation of said cylindrical reference element 15 has one translational degree of freedom. It can slide along the central line 43, determined by the center of projection 44 and the center of said energy emitting source 29. Sliding position is controlled by Z (FIG. 11). With further two rotational degrees of freedom ($\alpha$, $\beta$) the position of said virtual geometric representation of said cylindrical reference element 15 is fully constrained.

Four virtual projection points representing said two points of intersection 35, 36 and said first and second apex 37, 38 are derived from the orientation of said virtual geometric representation of said cylindrical reference element 15.

A numerical optimization routine is used to find a global minimum for the deviations between said significant landmarks the actual projection points and the corresponding virtual projection points using three degrees of freedom (DOF) ($\alpha$, $\beta$, Z) in order to carry out the optimized orientation of said virtual geometric representation of said cylindrical reference element 15. Due to the asymmetry of the lens-shaped projection 42 (segments b and c appear asymmetrically, due to the nature of a central projection) it is possible to calculate a unique solution for the orientation of the cylindrical reference element 15 from a single image.

The procedure can be extended by use of a plurality of circular cylindrical reference elements 15 with known distances and alignment to each other. The entirety of all deviations between virtual and actual projection landmarks of all cylindrical reference elements 15 is numerically minimized over said three degrees of freedom. This approach has the following advantages:

a) the position of an object comprising a set of circular cylindrical reference elements 15 (at least two) can be tracked in 6 degrees of freedom and is thereby fully constrained.

b) Taking distances between center points 47 of cylindrical reference elements 15 into account increases the accuracy of determining the Z-dimension.

c) With additional redundant landmarks in the equation, the accuracy of the procedure increases and the risk of the algorithm converging to wrong solutions (local minima) decreases.

Numerical Procedure to Determine the Spatial Position of an Unconstrained Target Structure From Two Oblique Projections With Respect to a Set of Cylindrical Reference Means When aiming at reconstructing the position in space of a significant landmark within an X-ray projection, such as a vertex or edge of a bone or the center of a femoral/humeral head, the previously described procedure can be used in the following way:

1. Acquiring two oblique medical images 50 of the target structure and of a set of cylindrical reference elements 15 under the precondition that target structure and cylindrical reference elements 15 remain at a static position during imaging.

2. Detecting a significant landmark of the target structure and the projection of the set of cylindrical reference elements 15 in both medical images 50.

3. Determining the spatial position and orientation of the set of cylindrical reference elements 15 in both medical images 50 in coordinates of a local coordinate system 24 (COS) rigidly bonded with the radiographic device by using the previously described procedure.

4. Determining the relation between both local COS in a global set of coordinates rigidly bonded with the set of cylindrical reference elements 15.

5. Transforming the line determined by the projected landmark of the target structure to the center of the energy emitting source 29 of the radiographic device into the global system of coordinates for both medical images 50.

6. The point of intersection of both lines defines the spatial position of the landmark of the target structure with respect to the set of cylindrical reference elements 15.

It should be understood that the procedure can be extended by increasing the number of oblique projections. More images allow more accurate 2D-3D conversion of more complex geometrical structures. However, this increases at the same time the complexity of the procedure and the radiation exposure to the operator, to the operating room personnel and to the patient.

The above method and numerical procedure have been described with the use of one or more medical images 50 obtained by means of a radiographic device. The method and numerical procedure can be similarly applied to medical images 50 obtained by means of a photo/video camera.

Applications of the Invention

The above specified tracking system can be used in various medical fields, e.g. general trauma, spine, maxillofacial, pelvis. In the following exemplary applications in orthopedic and trauma surgery are briefly described:

Example 1: Distal Interlocking of Intramedullary Nails

One reference device 1 is attached to an aiming arm (outside of the human body) and should be visible in medio-lateral radiographs from the distal region after nail insertion. This allows localization of the nail holes in relation to the reference device 1. For drilling the interlocking holes in the bone, the drill is placed and aligned in relation to the reference device 1, so that the desired drill trajectory hits the holes in the nail. The camera device for determining the trajectory can be mounted directly on the drill or an additional reference device 1 can be attached to the drill and a camera device captures both reference devices 1.

Example 2: Drilling in General and Screw Placement

Similar to application 1 the approach can be used in various drilling and screw placement procedures, e.g. SI screw placement, lag screw positioning in the femoral head.

Example 3: Hip Cup Positioning

Anatomical Landmarks are Selected from Radiographs and their Positions are Determined in relation to the reference device 1. Cup position, inclination and anteversion angle can be computed and continuously observed via a camera device.

Example 4: Fusion or Registration of Images

A further possibility is the fusion or registration of images for augmented reality and mixed reality applications, e.g. tracking and visualization of a needle.

Example 5: Corrective Osteotomies (Tracking Bone Fragments by an Optical Camera)

Each a reference device 1 is attached to the proximal and distal part of the planned osteotomy. The reference devices 1 are captured continuously by an optical camera device and the achieved amount of correction is determined by relative deviation between both reference devices 1. The camera device can be mounted on the C-arm, included in the OR lamp or can be part of other devices like smartphones, tablets or smart glasses.

Example 6: Fracture Reduction

This application works very similar to the previous example.

An exemplary embodiment of the method for real-time tracking of bone and/or surgical objects in computer-assisted surgery according to the invention comprises the following steps: I) temporarily positioning at least one medical implant, surgical instrument and/or surgical tool equipped with a reference device 1 as described above with respect to an anatomical structure; II) capturing the at least one reference device 1 by means of a photo/video camera device in at least one medical image; III) calculating the spatial orientation and position of the at least one reference device 1 with respect to a camera based system of coordinates using data from the medical image; IV) transforming the derived orientation and position into a local system of coordinates; and V) transmitting the derived orientation and position information to a display means.

In step III) the calculation of the spatial orientation and position of the at least one reference device 1 with respect to a camera based system of coordinates using data from the medical image comprises the following steps:

i) automatically detecting a lens-shaped projection 42 of a cylindrical reference element 15 arranged in the at least one reference device 1 and determining of significant landmarks by use of image processing algorithms;

ii) simulating a virtual geometric representation of the cylindrical reference element 15 and of virtual projection points corresponding to the landmarks;

iii) iteratively optimizing the angular orientation and position of the virtual geometric representation by means of a numerical optimization routine to determine the actual spatial position and orientation of the cylindrical reference element 15; and iv) calculating the spatial orientation and position of the at least one reference device 1 by finding a unique solution for a system of cylindrical reference means.

Exemplarily but not limiting, step II) can be performed by obtaining the medical image by capturing the screen of a medical radiographic device by using a photo/video camera. Furthermore, step II) can additionally involve the sub-steps of taking at least one X-ray image of the at least one reference device 1 and the anatomical structure.

Additionally, step IV) can comprise the sub-step of establishing an anatomy based system of coordinates based on the at least one X-ray image. The orientation and position values of the at least one reference device 1 can then additionally or alternatively be transformed into the anatomy based system of coordinates. Preferably, the anatomy based system of coordinates can be established by manually selecting anatomical landmarks. Alternatively or additionally, the orientation and position of the reference device 1 can be transformed into coordinates defined by the orientation and position of a second reference device 1. Alternatively or additionally, the orientation and position values of the at least one reference device 1 can be transformed into a system of coordinates derived from an earlier iteration of the method according to the invention.

Preferably, steps II)-IV) are iteratively repeated to create redundant information. Furthermore, step III) can be repeated after changing the view angle of the medical image.

The display means used in step V) can be a screen which is integrated in one of a smartphone, a tablet computer, a smart glass, a personal computer and a head mounted display. Furthermore, the implant position can be exemplarily visualized by augmenting the X-ray image with a geometric representation of the implant in its current position.

Exemplarily but not limiting, the camera device can be attached to or integrated in one of a surgical instrument, a surgical power drill, an X-ray device, an OR-light, a smartphone, a tablet computer, a smart glass and a head mounted display.

Furthermore, the method according to the invention can include the additional step of measuring angles between bone fragments during a surgical fracture reduction or during corrective osteotomies.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A reference device for real-time tracking of bone and/or surgical objects in computer-assisted surgery, the device comprising:
    an upper member having an upper surface, a lower surface and a plurality of circular cylindrical holes penetrating through the upper member such that each of the plurality of holes has an upper orifice at the upper surface of the upper member and a lower orifice at the lower surface of the upper member; and
    a lower member that covers the lower orifices of the plurality of holes;
    wherein each of the plurality of holes defines a circular cylindrical reference element having a diameter d and a height h,
    wherein a ratio between the diameter d and the height h of each of the reference elements is a minimum of 1:3,
    wherein the upper member is a plate shaped body,
    wherein the upper member comprises, at least at a periphery of the plurality of holes, a radiopaque, medical grade material selected from the group consisting of stainless steel, titanium and plastic, and
    wherein the lower member is made of a radiolucent material.

2. The reference device according to claim 1, wherein the reference device further comprises an attachment means for loosenably securing the reference device to one or more of a medical implant, surgical instrument, surgical tool and an operation table.

3. The reference device according to claim 1, wherein the reference device is integrated in one or more of a medical implant, a surgical instrument and a surgical tool.

4. The reference device according to claim 2, wherein the attachment means is a clamp or a clip or a threaded connection.

5. The reference device according to claim 1, wherein the reference device further comprises a locking mechanism for positioning and securing the reference device in a defined position relative to one or more of a medical implant, a surgical instrument and a surgical tool.

6. The reference device according to claim 1, wherein the lower member has an upper surface which has a different color and/or reflectance than the upper member.

7. The reference device according to claim 1, wherein the lower member is reflective or luminescent.

8. The reference device according to claim 1, wherein the lower member is attached to the lower surface of the upper member.

9. The reference device according to claim 1, wherein the lower member is offset with respect to the lower surface of the upper member.

10. The reference device according to claim 1, wherein the lower member is provided with a plurality of recesses, wherein each of said plurality of recesses has a concave shape that is configured to align with the lower orifice of a corresponding one of the plurality of holes at the lower surface of the upper member.

11. The reference device according to claim 1, wherein the upper member comprises an intermediate member which is arranged between the lower surface of the upper member and the lower member, and wherein the intermediate member is made from a transparent material.

12. The reference device according to claim 1, wherein first and second radiopaque sleeve sections are attached to an inner wall of each of the holes, the first sleeve section extending from the upper surface to a hollow space and the second sleeve section extending from the lower surface to a hollow space.

13. The reference device according to claim 1, wherein a central axis of at least one of the plurality of holes is askew relative to a central axes of another of the plurality of holes.

14. The reference device according to claim 1, wherein the upper member and the lower member are formed out of one piece, and wherein the plurality of holes are blind holes.

15. A tracking system for real-time tracking of bone and/or surgical objects in computer-assisted surgery, the tracking system comprising:
    one or more reference devices according to claim 1;
    a camera device or an X-ray device; and
    a processing unit provided with an image processing algorithm.

16. A method for real-time tracking of bone and/or surgical objects in computer-assisted surgery comprising steps of:
    I) temporarily positioning at least one medical implant, surgical instrument and/or surgical tool equipped with a reference device according to claim 1 with respect to an anatomical structure;
    II) capturing the at least one reference device by means of a photo/video camera device in at least one medical image;
    III) calculating a spatial orientation and position of the at least one reference device with respect to a camera based system of coordinates using data from the at least one medical image and by performing sub-steps of:
        i) automatically detecting a lens-shaped projection of the cylindrical reference element arranged in the at least one reference device and determining significant landmarks by use of image processing algorithms;
        ii) simulating a virtual geometric representation of the cylindrical reference element and of virtual projection points corresponding to the landmarks;
        iii) iteratively optimizing an angular orientation and position of the virtual geometric representation by means of a numerical optimization routine to determine an actual spatial position and orientation of the cylindrical reference element; and
        iv) deriving an actual spatial orientation and position of the at least one reference device by finding a unique solution for a system of cylindrical reference means;
    IV) transforming the derived actual spatial orientation and position of the at least one reference device into a local system of coordinates; and
    V) transmitting information depicting the derived actual spatial orientation and position of the at least one reference device to a display means.

17. The method according to claim 16, wherein step II) additionally involves taking at least one X-ray image of the at least one reference device and the anatomical structure.

18. The method according to claim 16, wherein step II) involves obtaining the medical image by capturing a screen of a medical radiographic device using a photo/video camera.

* * * * *